(12) United States Patent
Lee

(10) Patent No.: US 11,534,620 B2
(45) Date of Patent: Dec. 27, 2022

(54) MAGNETIC STIMULATION DEVICE HAVING PLANAR COIL STRUCTURE

(71) Applicant: Po-Lei Lee, Taipei (TW)

(72) Inventor: Po-Lei Lee, Taipei (TW)

(73) Assignee: Hsuan-Hua Chiu, Taoyuan (TW)

( * ) Notice: Subject to any disclaimer, the term of this patent is extended or adjusted under 35 U.S.C. 154(b) by 333 days.

(21) Appl. No.: 16/799,714

(22) Filed: Feb. 24, 2020

(65) Prior Publication Data

US 2021/0260396 A1 Aug. 26, 2021

(51) Int. Cl.
*A61N 2/02* (2006.01)
*A61N 2/00* (2006.01)
*A61N 1/40* (2006.01)
*G01R 33/36* (2006.01)

(52) U.S. Cl.
CPC .............. *A61N 2/02* (2013.01); *A61N 1/40* (2013.01); *A61N 2/006* (2013.01); *G01R 33/36* (2013.01)

(58) Field of Classification Search
CPC . A61N 2/02; A61N 1/40; A61N 2/006; G01R 33/36
USPC ........................................ 600/9–15
See application file for complete search history.

(56) References Cited

U.S. PATENT DOCUMENTS

| | | | | |
|---|---|---|---|---|
| 5,224,922 A * | 7/1993 | Kurtz | | A61N 2/02 600/13 |
| 5,480,373 A * | 1/1996 | Fischer | | A61N 2/02 600/14 |
| 2005/0171397 A1 * | 8/2005 | Baugh | | A61N 2/02 600/14 |
| 2011/0021863 A1 * | 1/2011 | Burnett | | A61N 2/006 600/13 |
| 2011/0178574 A1 * | 7/2011 | Hardy | | A61N 2/02 607/50 |
| 2012/0190989 A1 * | 7/2012 | Kaiser | | A61B 5/08 600/300 |
| 2013/0274542 A1 * | 10/2013 | Volo | | A61N 1/40 600/13 |

(Continued)

FOREIGN PATENT DOCUMENTS

| CN | 201510701763.3 | 10/2017 |
|---|---|---|
| TW | 1528984 | 4/2016 |

(Continued)

OTHER PUBLICATIONS

M.E. Maffei, Magnetic field effects on plant growth, development, and evolution, Frontiers in plant science. 5 (2014) 445.

(Continued)

*Primary Examiner* — Sunita Reddy
(74) *Attorney, Agent, or Firm* — Che-Yang Chen; Law Office of Michael Chen

(57) ABSTRACT

A magnetic stimulation device having planar coil structure is disclosed. It contains a power supply module, a current control module, a plurality of planar coil modules and a plurality of electrical connection modules. In the planar coil module of the present invention, the coil structure has a flat and thin design and can be modularized. Compared with the existing magnetic stimulation devices, the overall structure of the present invention is light, thin, short, convenient to carry and use, and can be installed on clothing or built in a mobile device to provide a convenient magnetic stimulation treatment.

12 Claims, 14 Drawing Sheets

(56) References Cited

U.S. PATENT DOCUMENTS

| | | | | |
|---|---|---|---|---|
| 2015/0080636 A1* | 3/2015 | Rogachefsky | ......... | A61B 17/72 600/13 |
| 2015/0080637 A1* | 3/2015 | Bonmassar | ............. | A61N 2/02 600/14 |
| 2018/0102030 A1* | 4/2018 | Khoshkava | ............ | H02K 35/00 |
| 2021/0251679 A1* | 8/2021 | Silva | ...................... | A61B 18/12 |
| 2021/0361965 A1* | 11/2021 | Yakobson | .............. | A61N 2/004 |

FOREIGN PATENT DOCUMENTS

| | | |
|---|---|---|
| TW | M562133 | 6/2018 |
| TW | 201922313 | 6/2019 |

OTHER PUBLICATIONS

A. Lerchl, et al., Marked rapid alterations in nocturnal pineal serotonin metabolism in mice and rats exposed to weak intermittent magnetic fields, Biochemical and biophysical research communications. 169 (1) (1990) 102-108.

J. Sabo, et al., Effects of static magnetic field on human leukemic cell line HL-60, Bioelectrochemistry. 56 (1-2) (2002) 227-231.

Shang Rong etc., Prevention and treatment of supraventricular arrhythmia with magnetic intradermal needle at Neiguan acupoint, 38 cases, Traditional Chinese Medicine Research 14 (4) (2001) 62-63.

L. Baker-Price, M.A. Persinger, Weak, but complex pulsed magnetic fields may reduce depression following traumatic brain injury, Perceptual and motor skills. 83 (2) (1996) 491-498.

J. Dobson, et al., Preliminary evidence for weak magnetic field effects on mechanosensitive ion channel subconducting states in *Escherichia coli*, Electromagnetic Biology and Medicine. 21 (1) (2002) 89-95.

Fang Feng, Shen Qian, Effect of magnetic traditional Chinese medicine external application on cellular immune function of susceptible children, Chinese Acupuncture 17 (1) (1997) 15-16.

Zhou Chuanyun, Zhang Ruixue, Preliminary Study on the Mechanism of Acupoint Magnetotherapy, Journal of Anhui College of Traditional Chinese Medicine 21 (3) (2002) 8-10.

* cited by examiner

MAGNETIC STIMULATION DEVICE HAVING PLANAR COIL STRUCTURE

FIELD OF THE INVENTION

The present invention relates to a magnetic stimulation device. More particularly, the present invention relates to a magnetic stimulation device having flattened planar coil structures which can be installed in clothing or built in a mobile device to provide a magnetic stimulation treatment for human body to improve physical condition.

BACKGROUND OF THE INVENTION

In recent years, due to the development of technologies in electromagnetic field, many studies on biological magnetic fields have begun to lead the trend. Research on biomagnetic fields has been applied in various fields, such as researches on promoting growth of plant seeds, organism health, etc. Some studies have also shown that weak magnetic fields can promote cell division and growth (M. E. Maffei, Magnetic field effects on plant growth, development, and evolution, Frontiers in plant science. 5 (2014) 445). In the research on mice, it was found that changes in magnetic fields can cause differences in metabolic rates (A. Lerchl, et al., Marked rapid alterations in nocturnal pineal serotonin metabolism in mice and rats exposed to weak intermittent magnetic fields, Biochemical and biophysical research communications. 169 (1) (1990) 102-108). In human studies, it has also been found that low-frequency constant magnetic fields can promote human white blood cells (J. Sabo, et al., Effects of static magnetic field on human leukemic cell line HL-60, Bioelectrochemistry. 56 (1-2) (2002) 227-231). Therefore, the application of magnetic fields has also set an important research direction in the scientific community. Magnetic stimulation is gradually gaining attention.

In the field of basic medical research, magnetic stimulation has the following results: 74% improvement in patients with abnormal heart rate when given magnetic intradermal needles at Neiguan acupoint (Shang Rong etc., Prevention and treatment of supraventricular arrhythmia with magnetic intradermal needle at Neiguan acupoint, 38 cases, Traditional Chinese Medicine Research 14 (4) (2001) 62-63); using low-pulse magnetic fields found to reduce depression in patients with brain trauma (L. Baker-Price, M. A. Persinger, Weak, but complex pulsed magnetic fields may reduce depression following traumatic brain injury, Perceptual and motor skills. 83 (2) (1996) 491-498); under the environment of 25 times the magnetic field of the earth, *Escherichia coli* cells increasing the sensitivity of their cell ion channels. (J. Dobson, et al., Preliminary evidence for weak magnetic field effects on mechanosensitive ion channel subconducting states in *Escherichia coli*, Electromagnetic Biology and Medicine. 21 (1) (2002) 89-95). In the study of traditional Chinese medicine, it was found that the use of magnetic traditional Chinese medicine can significantly improve the number of immune cells after 12 weeks of external application (Fang Feng, Shen Qian, Effect of magnetic traditional Chinese medicine external application on cellular immune function of susceptible children, Chinese Acupuncture 17 (1) (1997) 15-16). In the study of acupuncture magnetic fields, magnets were placed in acupuncture points of Neiguan, Zusanli, and Guanyuan for men and it was found that the amount and activity of sperm could be increased (Zhou Chuanyun, Zhang Ruixue, Preliminary Study on the Mechanism of Acupoint Magnetotherapy, Journal of Anhui College of Traditional Chinese Medicine 21 (3) (2002) 8-10). Therefore, we can know that using a low energy magnetic field has a good effect on physiological regulation.

As the research results of magnetic stimulation become more and more abundant, many commercialized technologies, such as Taiwan invention patent No. 1528984, utility model patent No. M562133, patent application No. 201922313, etc., also appear in front of people. These technologies have some common characteristics: they are bulky and expensive, making them difficult to carry at home or when going out. In addition, most of the existing technologies are about Repetitive Transcranial Magnetic Stimulation (rTMS). They have poor versatility. The reason is mainly due to the control of the magnetic field strength, and the volume of the magnetic stimulation generating device cannot be reduced. If it is desired to reduce the volume of the magnetic stimulation generating device, Chinese patent publication No. CN105242224, Close-contact type double layer plane radio frequency coil used for composite insulator detection, can be referred. However, the patent is applied to detect the material defect using two coils in radio frequency range, which was designed for the purpose different from our invention. In addition, the patent belongs to high frequency radiation, and cannot be applied to low-frequency current magnetic fields. The latter is a must for magnetic stimulation.

Hence, to implement the results of magnetic stimulation research in life and improve people's health, there must be a miniaturized magnetic stimulation device so that people can use it with better operation experience. Preferably, the coil of this magnetic stimulation device can be flat and modularized, further being installed on clothing or built into a mobile device and becoming a part of life.

SUMMARY OF THE INVENTION

This paragraph extracts and compiles some features of the present invention; other features will be disclosed in the follow-up paragraphs. It is intended to cover various modifications and similar arrangements included within the spirit and scope of the appended claims.

In order to fulfill the requirement above, a magnetic stimulation device having coil structure is disclosed in the present invention. The magnetic stimulation device having coil structure comprises: a power supply module, providing electric power; a current control module, electrically connected with the power supply module, comprising: a signal generator, generating a current waveform signal; and a current switch, electrically connected with the signal generator, adjusting a waveform of the current from the power supply module with the current waveform signal to form an adjusted output current; and at least one planar coil module, comprising: a first insulating substrate; and a planar coil, formed on the first insulating substrate where two ends of the planar coil and the current switch form a loop, receiving the adjusted output current to generate a corresponding varying intensity magnetic field. If the number of the planar coil module is one, the planar coil is directly electrically connected with the current switch. If the number of the planar coil module planar coil module is more than one, end points of the planar coils of adjacent two planar coil modules are connected and unconnected endpoints of the planar coils of the first and the last planar coil modules are directly electrically connected with the current switch.

Another magnetic stimulation device having coil structure is also disclosed in the present invention. The magnetic stimulation device having coil structure comprises: a power supply module, providing electric power; a current control module, electrically connected with the power supply module, comprising: a signal generator, generating a current waveform signal; and a current switch, electrically connected with the signal generator, adjusting a waveform of the current from the power supply module with the current waveform signal to form an adjusted output current; and at least one planar coil module, comprising: at least one first insulating substrate; and a plurality of planar coils, parallel to one another, wherein adjacent two planar coils are electrically connected and formed on two sides of the same first insulating substrate. If the number of the planar coil module is one, end points of the outermost two planar coils are directly electrically connected with the current switch to form a loop. If the number of the planar coil module is more than one, end points of the outermost planar coils of adjacent two planar coil modules are connected and unconnected endpoints of the outermost planar coils of the first and the last planar coil modules are directly electrically connected with the current switch. The planar coil receives the adjusted output current to generate a corresponding varying intensity magnetic field, the current in the plurality of planar coils of the same planar coil module flows in the same rotational direction, and locations of the strongest magnetic field intensity generated by current of every planar coils are substantially aligned.

Preferably, the planar coil module further may comprise a ferrite core, located on location of the strongest magnetic field intensity generated by current of the planar coil module, enhancing the overall magnetic permeability of the planar coil module.

Preferably, the current control module may further comprise a current limiter, electrically connected between the power supply module and the current switch, limiting the current from the power supply module.

Preferably, adjacent two planar coils are electrically connected by plating through a via hole formed on the first insulating substrate.

Preferably, the power supply module may comprise at least one primary battery, at least one secondary battery or a power supply.

Preferably, the signal generator may be a waveform generator, a pulse generator or a clock generator.

Preferably, a waveform of the current waveform signal may be a sine wave, a half sine wave, a pulse wave or a fixed waveform.

Preferably, the planar coil may be made by etching metal foil, winding metal wire or printing conductive adhesive.

Preferably, a material of the first insulating substrate may be bakelite, cotton paper, epoxy resin, glass cloth, glass fiber, phenolic resin, glass, polyimide or polyester.

The magnetic stimulation device having coil structure may further comprise a plurality of electrical connection modules, electrically connected with the planar coil module and the current switch to form a loop. Each electrical connection module comprises: a second insulating substrate; at least one wire, formed on the second insulating substrate; and a waterproof protective layer, covering the at least one wire and the second insulating substrate to protect the at least one wire and avoid damages from external water.

Preferably, a material of the second insulating substrate may be polyimide or polyester.

Preferably, a material of the waterproof protective layer may be polyimide film or polyethylene terephthalate film.

According to the present invention, the planar coil is formed around a specific pattern. An electric stimulation magnetic field of the planar coil module generated by the adjusted output current generally ranges from 0 to 1000 Gauss.

The coil structure in the present invention has a flat and thin design and can be modularized. Compared with the existing magnetic stimulation devices, the overall structure of the present invention is light, thin, short, convenient to carry and use, and can be installed on clothing or built in a mobile device to fulfill the requirement above.

DETAILED DESCRIPTION OF THE PREFERRED EMBODIMENTS

The present invention will now be described more specifically with reference to the following embodiments.

Figure 1:
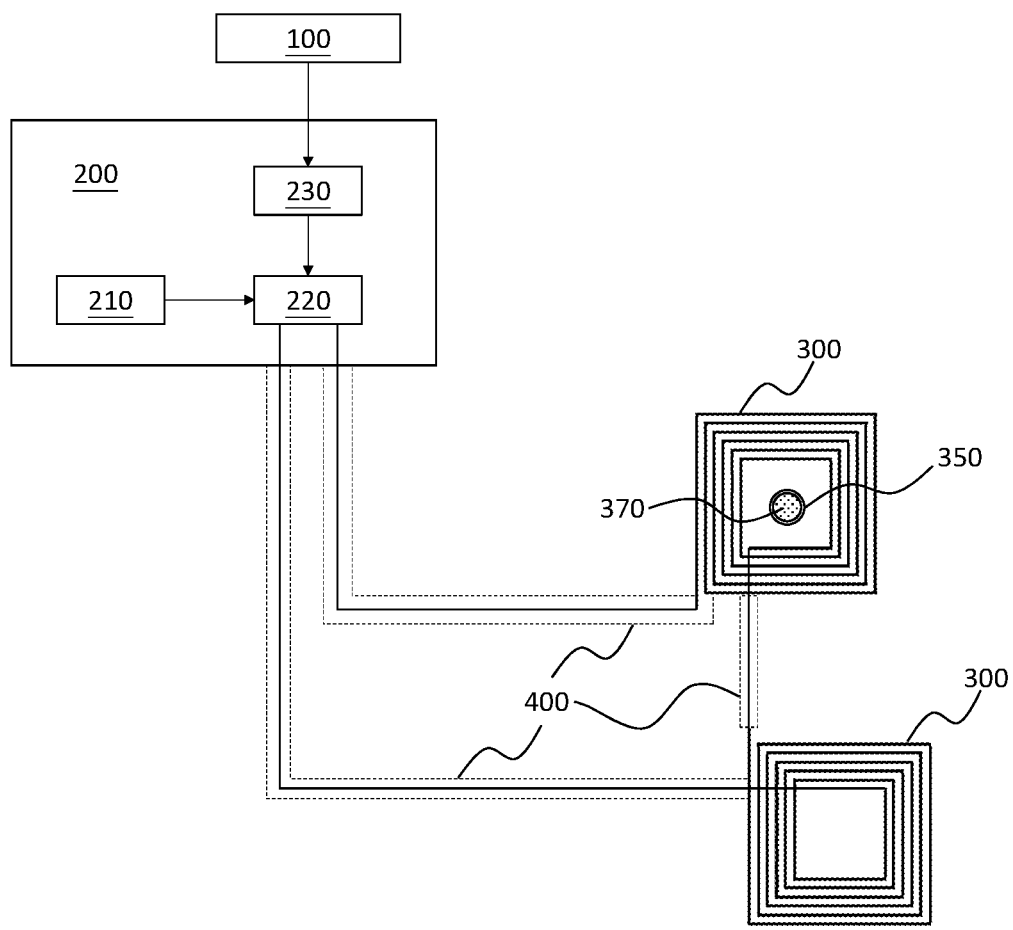
FIG. 1 is a system block diagram of a magnetic stimulation device having planar coil structure according to an embodiment of the present invention.

Please refer to FIG. 1. It is a system block diagram of a magnetic stimulation device having planar coil structure according to an embodiment of the present invention. The magnetic stimulation device having planar coil structure comprises: a power supply module 100, a current control module 200, 2 planar coil modules 300 and 3 electrical connection modules 400. The composition, function and mutual operation of each module will be explained in detail below.

The power supply module 100 is the main element that provides electric power. According to the spirit of the present invention, the electric power provided by the power supply module 100 can be either DC or AC. In terms of type, the power supply module 100 may be a battery case, comprising at least one primary battery, such as alkaline battery or mercury battery, or at least one secondary battery, such as lithium battery. More than two batteries can provide electric power in parallel or in series. The power supply module 100 may also be a power supply, using a transformer to convert power from the public grid to DC power, or even provide step-down AC power directly.

The current control module 200 is electrically connected with the power supply module 100 and comprises: a signal generator 210, a current switch 220 and a current limiter 230. The function of the signal generator 210 is to generate a current waveform signal. The waveform of the current waveform signal can be a periodic waveform, such as sine wave, half sine wave or pulse wave. The waveform of the current waveform signal can also be a fixed waveform, and the waveform remains essentially unchanged for a period of time. In some embodiments, a periodic wave or non-periodic wave at a high frequency (for example, 1 MHz) can be further modulated by the aforementioned basic waveform. According to the present invention, the signal generator 210 may be a waveform generator, a pulse generator or a clock generator. In the present embodiment, the current control module 200 is a waveform generator. In terms of type, the current control module 200 may be a single chip microcomputer, set according to a preset program or received external programmable pulses or waveforms. The programmable waveform generator can control the current switch 220 to produce the desired current waveform.

As described above, the current switch 220 and the signal generator 210 are electrically connected. The current switch 220 adjusts a waveform of the current from the power supply module 100 with the current waveform signal to form an adjusted output current. Namely, the adjusted output current itself has a waveform, such as sine wave, half sine wave or pulse wave, that changes over time, or it is a fixed current for a period of time.

The current limiter 230 is electrically connected between the power supply module 100 and the current switch 220, limiting the current from the power supply module 100. The current limiter 230 is a protection circuit that allows a certain amount of current flowing into the current control module 200. Its purpose is to protect users. However, in other embodiments, because the power supply module 100 has a small amount of current, the current limiter 230 can also be omitted and the power supply module 100 electrically connected with the current switch 220 directly.

Figure 2:
FIG. 2 is a schematic sectional view of a planar coil module.

Please refer to FIG. 2. It is a schematic sectional view of a planar coil module 300. The planar coil module 300 comprises a first insulating substrate 310, a planar coil 320 and a waterproof protective layer 330 covering a portion of the planar coil 320 and a portion of the first insulating substrate 310. The planar coil 320 is formed on the first insulating substrate 310, protected by the waterproof protective layer 330 and is free from rusting. According to the spirit of the present invention, the planar coil module 300 may be in the form of a printed circuit board (may be general type or flexible type). Therefore, the planar coil 320 may be made by etching metal foil or printing conductive adhesive. The material of the first insulating substrate may be, but not limited to bakelite, cotton paper, epoxy resin, glass cloth, glass fiber, phenolic resin, glass, polyimide or polyester. In addition, the planar coil module 300 may also not be in the form of a printed circuit board. The planar coil 320 can be formed by winding metal wire and fixed on the first insulating substrate 310. At this moment, the material of the first insulating substrate 310 is not limited to the foregoing. Many non-metallic and electrically insulating materials can be used.

Figure 3:
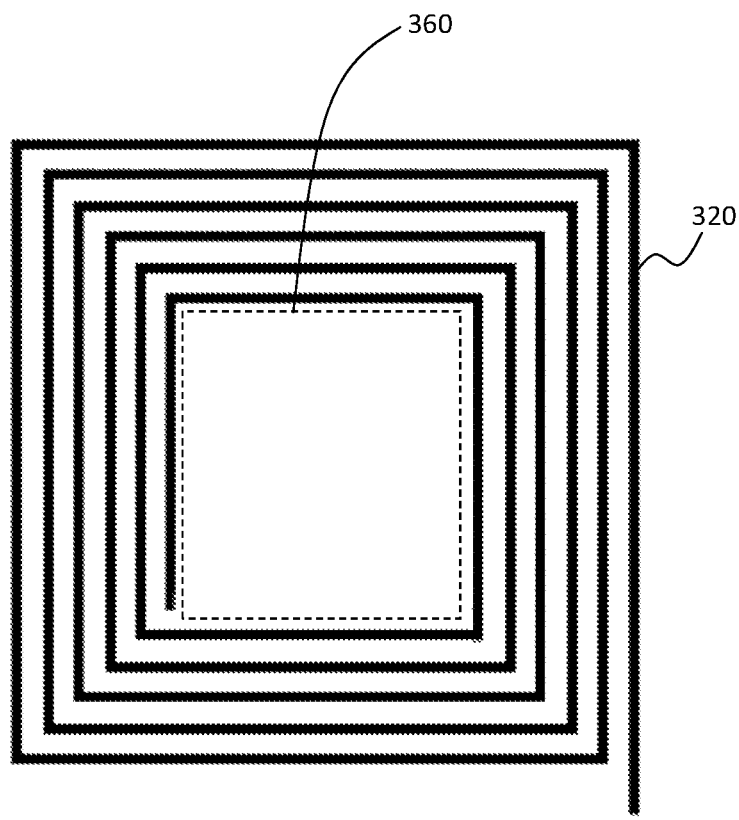
FIG. 3 shows a magnetic stimulation area generated inside a planar coil.
Figure 4:
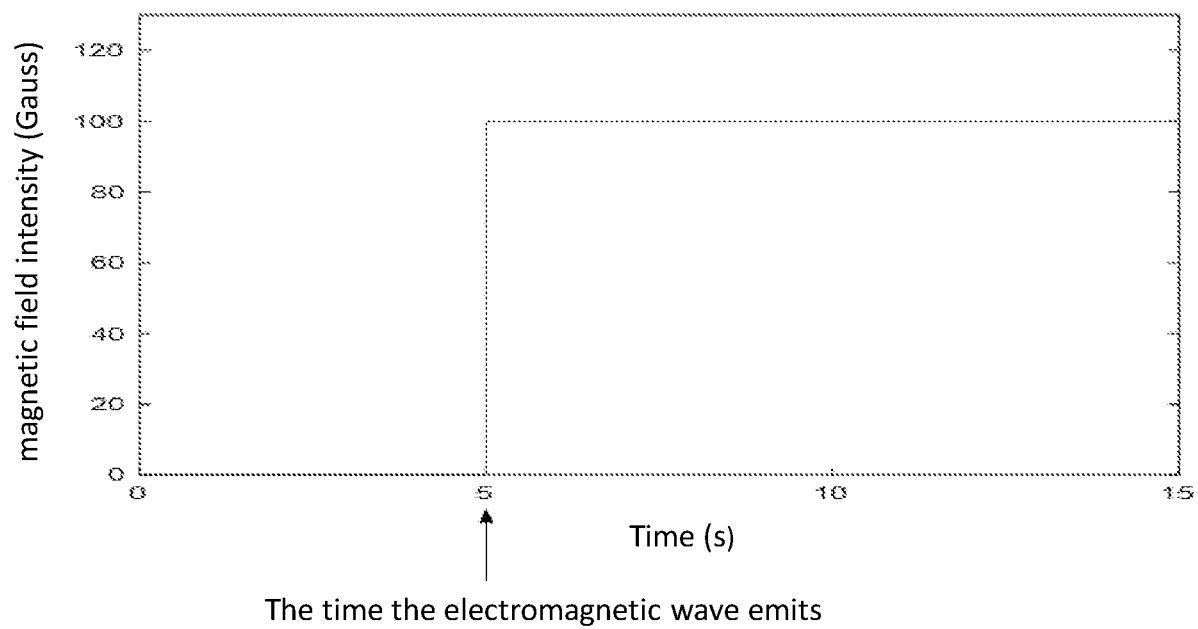
FIG. 4 shows change of the magnetic field intensity caused by a fixed waveform current over time.
Figure 5:
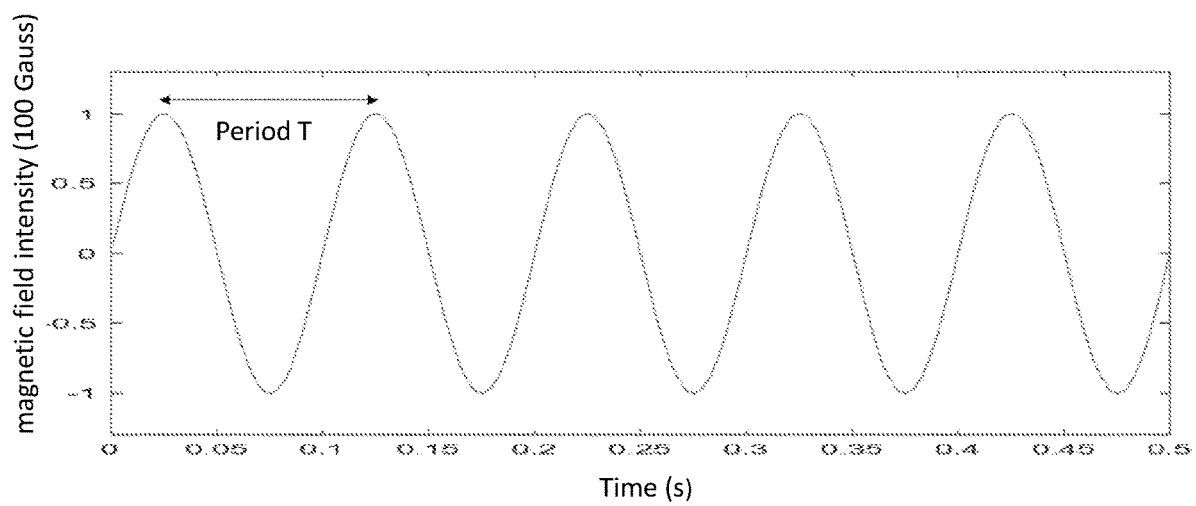
FIG. 5 shows change of the magnetic field intensity caused by a sine wave current over time.
Figure 6:
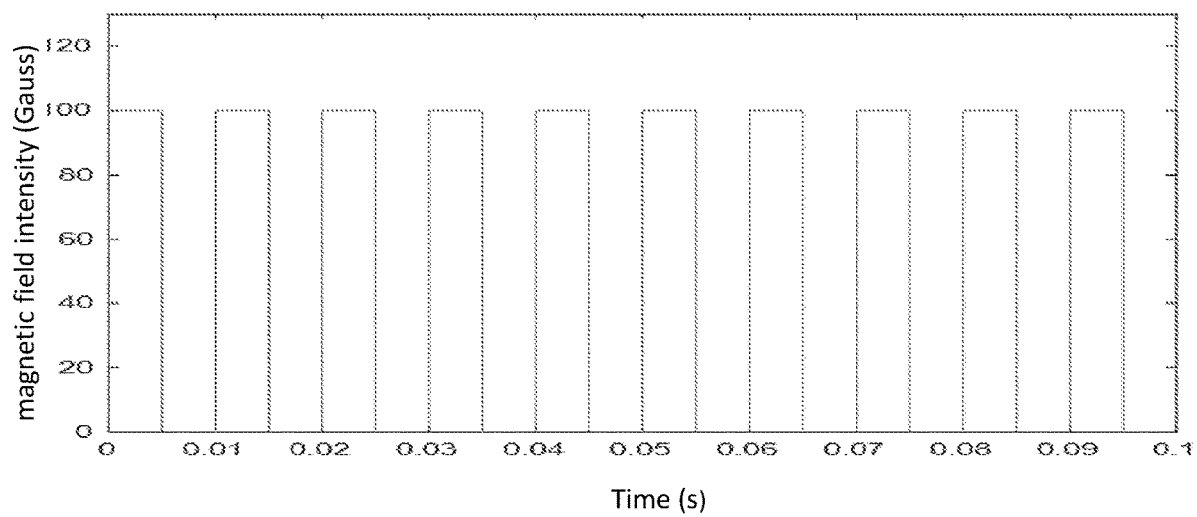
FIG. 6 shows change of the magnetic field intensity caused by a pulse wave current over time.
Figure 7:
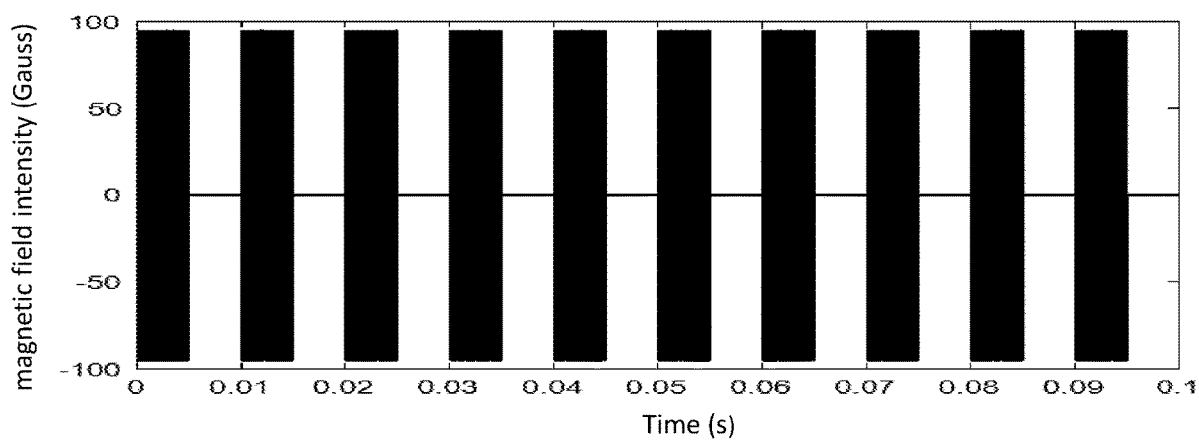
FIG. 7 shows change of the magnetic field intensity caused by a high frequency wave modulated with a pulse wave current over time.

Two end of the planar coil 320 and the current switch 220 forms a loop. The planar coil 320 receives the adjusted output current to generate a corresponding varying intensity magnetic field (an induced magnetic field). Please refer to FIG. 3. It shows a magnetic stimulation area 360 generated inside the planar coil 320. Body part facing the magnetic stimulation area 360 is the area that receives magnetic stimulation. Due to different coil winding shapes, there is a location 350 of the strongest magnetic field intensity generated by current, as shown in FIG. 1, in magnetic stimulation area 360. Intensity of the magnetic field at that area can be referred to the solenoid field formula, $B=\mu_0 NI$, where $\mu_0$ is air permeability ($4\pi \times 10^{-7}$ TmA$^{-1}$), N is the number of coils and I is the current intensity. Under the same current intensity, increasing the number of coils of the planar coil 320 can increase the magnetic field intensity. Magnetic field intensity of the area outside the location 350 of the strongest magnetic field intensity generated by current but inside the magnetic stimulation area 360 might be smaller than the value from the formula above. For all locations in the magnetic stimulation area 360, change of the magnetic field intensity at each place will vary depending on the waveform of the adjusted output current itself. FIG. 4 shows change of the magnetic field intensity caused by a fixed waveform current over time. For the emission in the magnetic field, the maximum magnetic field intensity is about 100 Gauss. According to the past literatures, low energy fixed magnetic field (0.about.1000 Gauss) has a curative and stimulative effect on living organisms. Therefore, in all embodiments of the present invention, an electric stimulation magnetic field of the planar coil module generated by the adjusted output current ranges from 0 to 1000 Gauss. FIG. 5 shows change of the magnetic field intensity caused by a sine wave current over time. For the emission in the magnetic field, the magnetic field intensity changes in a way of sine wave, between +100 Gauss and −100 Gauss with time. A fixed period is 0.01 second. A 100 Hz low frequency fixed frequency sine wave magnetic field is emitted. If the sine wave current is changed to a half sine wave current, the magnetic field intensity change will be correspondingly between 0 and −100 Gauss, or between 0 and +100 Gauss. FIG. 6 shows change of the magnetic field intensity caused by a pulse wave current over time. For the emission in the magnetic field, the maximum magnetic field intensity is around 100 Gauss. A fixed signal period is 0.01 seconds. A pulsed magnetic field with low frequency (100 Hz) is emitted. Effective duty cycle per emission is 50%. The implementation of the duty cycle can be adjusted through the signal generator 210 depending on the application requirements (referring to FIG. 1). FIG. 7 shows change of the magnetic field intensity caused by a high frequency wave modulated by a pulse wave current over time. For the emission in the magnetic field, a fixed magnetic field intensity is .+−0.95 Gauss. A fixed period is 0.01 second. Radio frequency magnetic field is emitted with a low frequency (100 Hz) signal period. Duty cycle per emission is 50%. The RF frequency in this example is 1 MHz (modulate high-frequency wave). Between each valid emission cycle (shown with black stripes), the magnetic field quickly oscillates between −95 Gauss and +95 Gauss according to the modulation waveform.

According to the present invention, the number of the planar coil module 300 can be at least one. If the number of the planar coil module 300 is one, the planar coil 320 is directly electrically connected with the current switch 220. If the number of the planar coil module is more than one (as shown in FIG. 1), end points of the planar coils 320 of adjacent two planar coil modules 300 are connected and unconnected endpoints of the planar coils of the first and the last planar coil modules 300 are directly electrically connected with the current switch 220.

In addition, the planar coil module 300 can comprise a ferrite core 370 located on the location 350 of the strongest magnetic field intensity generated by current of the planar coil module 300, enhancing the overall magnetic permeability of the planar coil module 300 to enhance the magnetic field intensity. The ferrite core 370 can be optionally installed in any planar coil module 300 according to actual needs.

Figure 8:
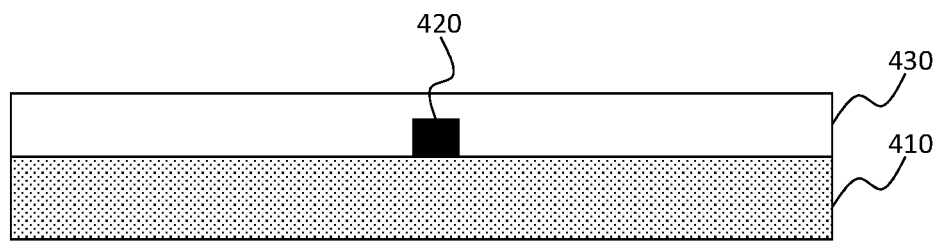
FIG. 8 is a sectional view of an electrical connection module.

According to the present invention, the number of the electrical connection module 400 is not restricted. It changes with the number of planar coil module 300. The electrical connection module 400 electrically connected with the planar coil module 300 and the current switch 220 to form a loop. In practice, a most basic form of the electrical connection module 400 is a wire. A better way is to use a flexible printed circuit board-like approach. Hence, please refer to FIG. 8. It is a sectional view of an electrical connection module. In the present embodiment, each electrical connection module 400 comprises a second insulating substrate 410, at least one wire 420 and a waterproof protective layer 430. The wire 420 is formed on the second insulating substrate 410. Similar to the planar coil 320, the wire 420 can be formed on the second insulating substrate 410 by etching metal foil or printing conductive adhesive. A material of the second insulating substrate 410 may be, but not limited to polyimide or polyester. The waterproof protective layer 430 (As shown by the dotted line in FIG. 1), covers the wire 420 and the second insulating substrate 410 to protect the at least one wire 420 and avoid damages from external water. A material of the waterproof protective layer 430 may be polyimide film or polyethylene terephthalate film. In terms of type, if all planar coil modules 300 and electrical connection modules 400 are made on the same second insulating substrate 410, it is possible to form interconnected circuits with copper foil. Now, the number of the electrical connection module 400 can be deemed as 1. However, considering practicality, the planar coil modules 300 need to be located on some specific locations, such as acupoints, to provide effects to improve physical health. Hence, electrical connections between the planar coil modules 300, between the planar coil module 300 and the current control module 200, even between the current control module 200 and the power supply module 100 are all implemented by the electrical connection module 400, respectively.

In the foregoing embodiments, there is only one planar coil in a planar coil module. However, according to the spirit of the present invention, the number of the planar coils in each planar coil module can be more than one. The planar coils are laminated in parallel to one another. The advantage of this is that in a limited area of the planar coil module, more planar coils are formed in a three-dimensional manner, enhancing the magnetic field intensity generated by the planar coil module. Please refer to FIG. 9. Here is another embodiment of a magnetic stimulation device with a planar coil structure.

Figure 9:
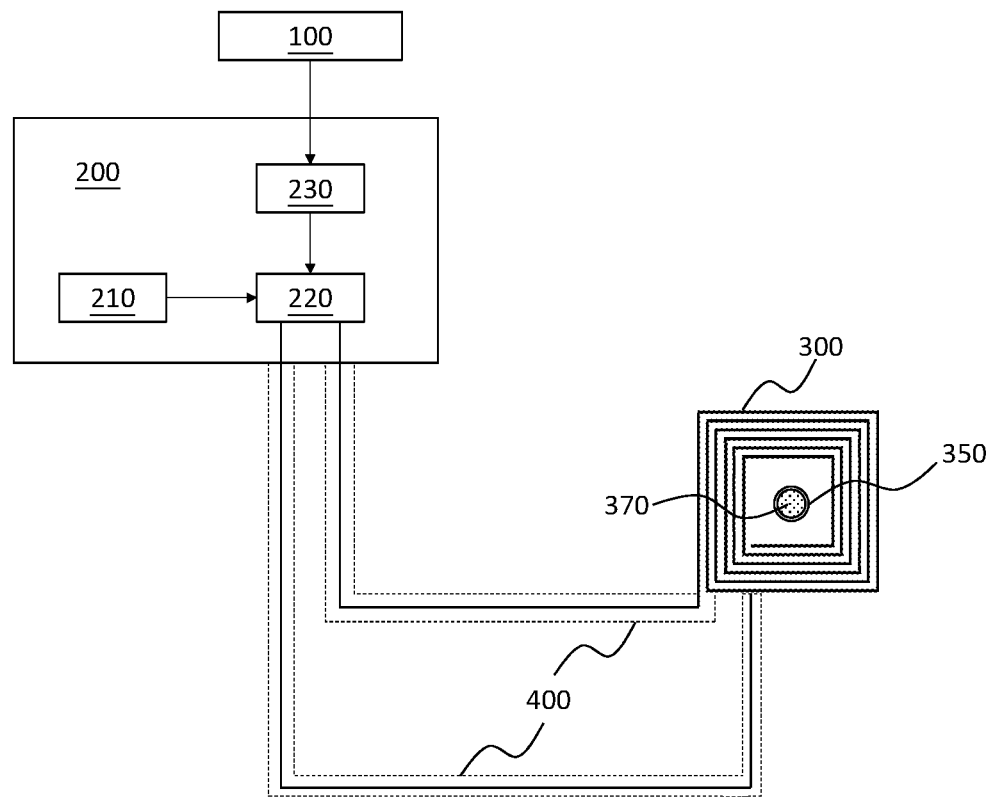
FIG. 9 is a system block diagram of a magnetic stimulation device with planar coil structure according to another embodiment of the present invention.
Figure 10:
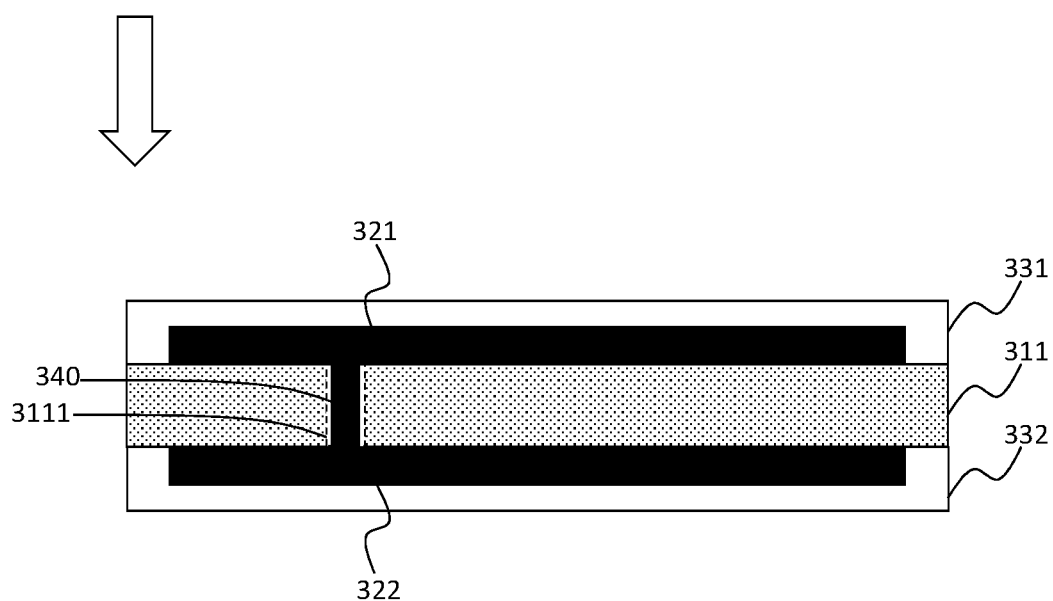
FIG. 10 is a sectional view of a planar coil module of another embodiment.

The magnetic stimulation device having planar coil structure in FIG. 9 is similar to the architecture in the previous embodiment, the difference is that the planar coil module 300 used in this embodiment has 2 planar coils. There is only one planar coil module 300. Thus, the number of electrical connection module 400 becomes 2. To simplify the description, the type and functions of the power supply module 100, the current control module 200, and the electrical connection module 400 are as described above. It is not repeated again. It should be emphasized that the number of the planar coil module 300 is at least one. It is not restricted by the present embodiment to be one. Please refer to FIG. 10. It is a sectional view of the planar coil module 300 of this embodiment. The planar coil module 300 comprises a first insulating substrate 311, a first planar coil 321, a second planar coil 322, a first waterproof protective layer 331 and a second waterproof protective layer 332. The first planar coil 321 and the second planar coil 322 are parallel to each other. They are adjacently electrically connected and formed on two sides of the first insulating substrate 311. Electrical connection is achieved by plating a via hole 3111 formed on the first insulating substrate 311 with a plating material 340.

Figure 11:
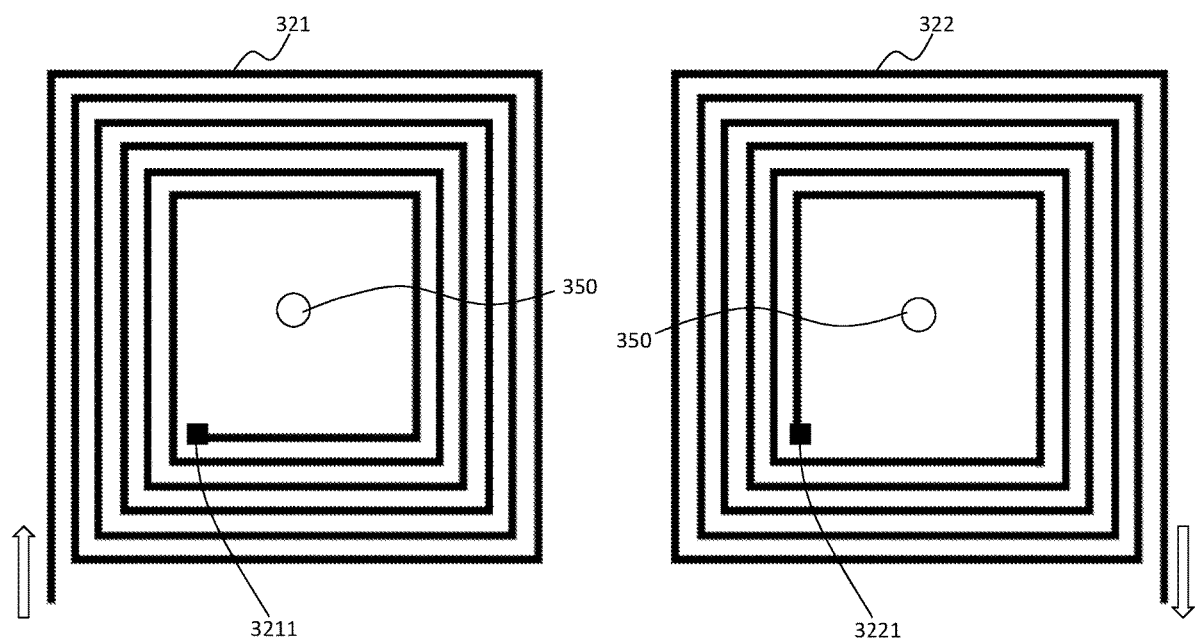
FIG. 11 is a schematic diagram showing a first planar coil and a second planar coil viewed along the direction of an arrow in FIG. 10.

In the present embodiment, the number of the planar coil module is one. End points of the first planar coil 321 and the second planar coil 322 are directly electrically connected with the current switch 220 to form a loop. The function of the first planar coil 321 and the second planar coil 322 is to receive the adjusted output current to generate a corresponding varying intensity magnetic field. It should be noticed that the technical characteristics of the present invention are the current in the plurality of planar coils of the same planar coil module flows in the same rotational direction, and locations of the strongest magnetic field intensity generated by current of every planar coils are substantially aligned. In order to have a better understanding of the technical characteristics, please refer to FIG. 11. It is a schematic diagram showing the first planar coil 321 and the second planar coil 322 viewed along the direction of an arrow in FIG. 10. The current flows in from the endpoint in the direction of the arrow on the left of the first planar coil 321 and flows out in a clockwise direction from an inner endpoint 3211 of the first planar coil 321. Since the inner endpoint 3211 and an inner endpoint 3221 of the second planar coil 322 are electrically connected, the current flows into the inner endpoint 3221 in a clockwise direction and flows out from the endpoint of the second planar coil 322 near the right arrow. Each planar coil receives the adjusted output current to generate a corresponding varying intensity magnetic field. Because the current directions of the upper and lower planar coils are the same, the magnetic field intensity is the addition of the two. Since the locations 350 of the strongest magnetic field intensity generated by current are substantially aligned (vertical direction), magnetic field lines will not interfere with each other to reduce the overall magnetic field intensity. Preferably, the location 350 of the strongest magnetic field intensity generated by current may be installed with one ferrite core to enhance the overall permeability of the planar coil module 300.

In the foregoing embodiments, the planar coil module has one or two planar coils. But in practice, there can be more planar coils. Such an example will be illustrated by the following embodiment.

Figure 12:
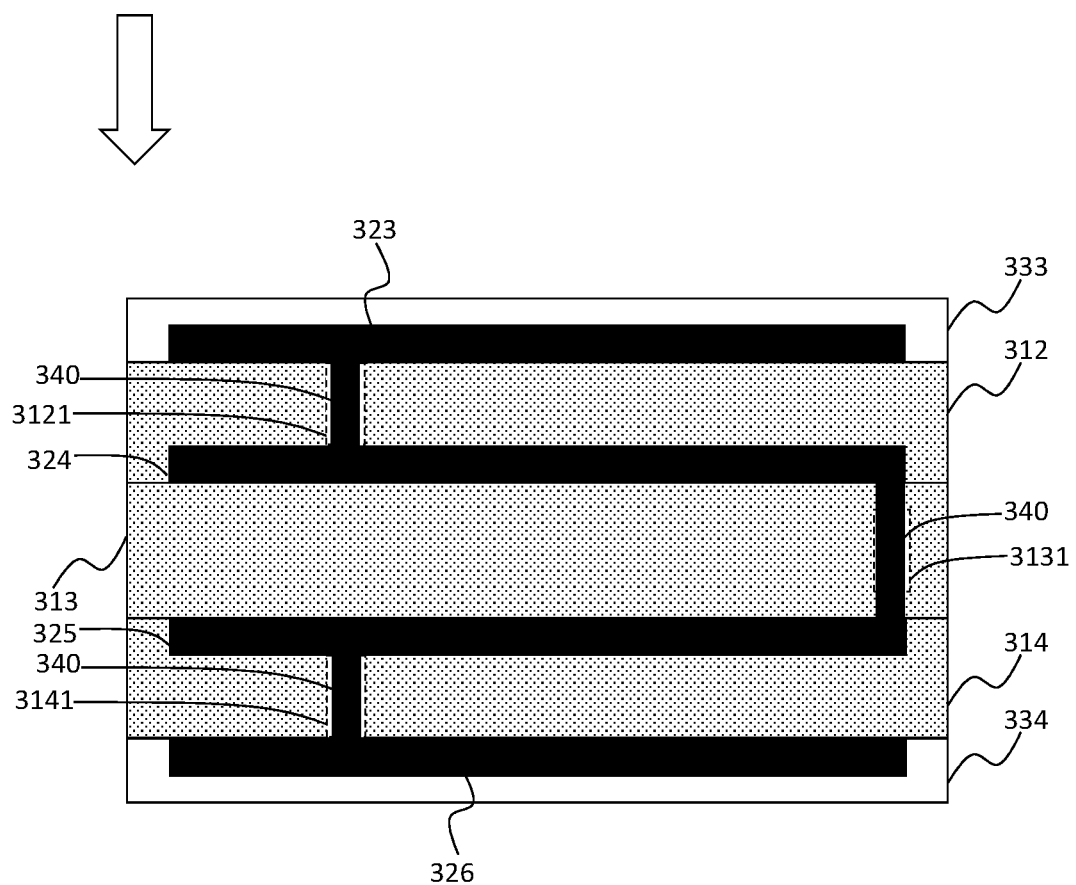
FIG. 12 is a sectional view of the structure of different planar coil modules under the structure of the magnetic stimulation device with planar coil structure in FIG. 1.
Figure 13:
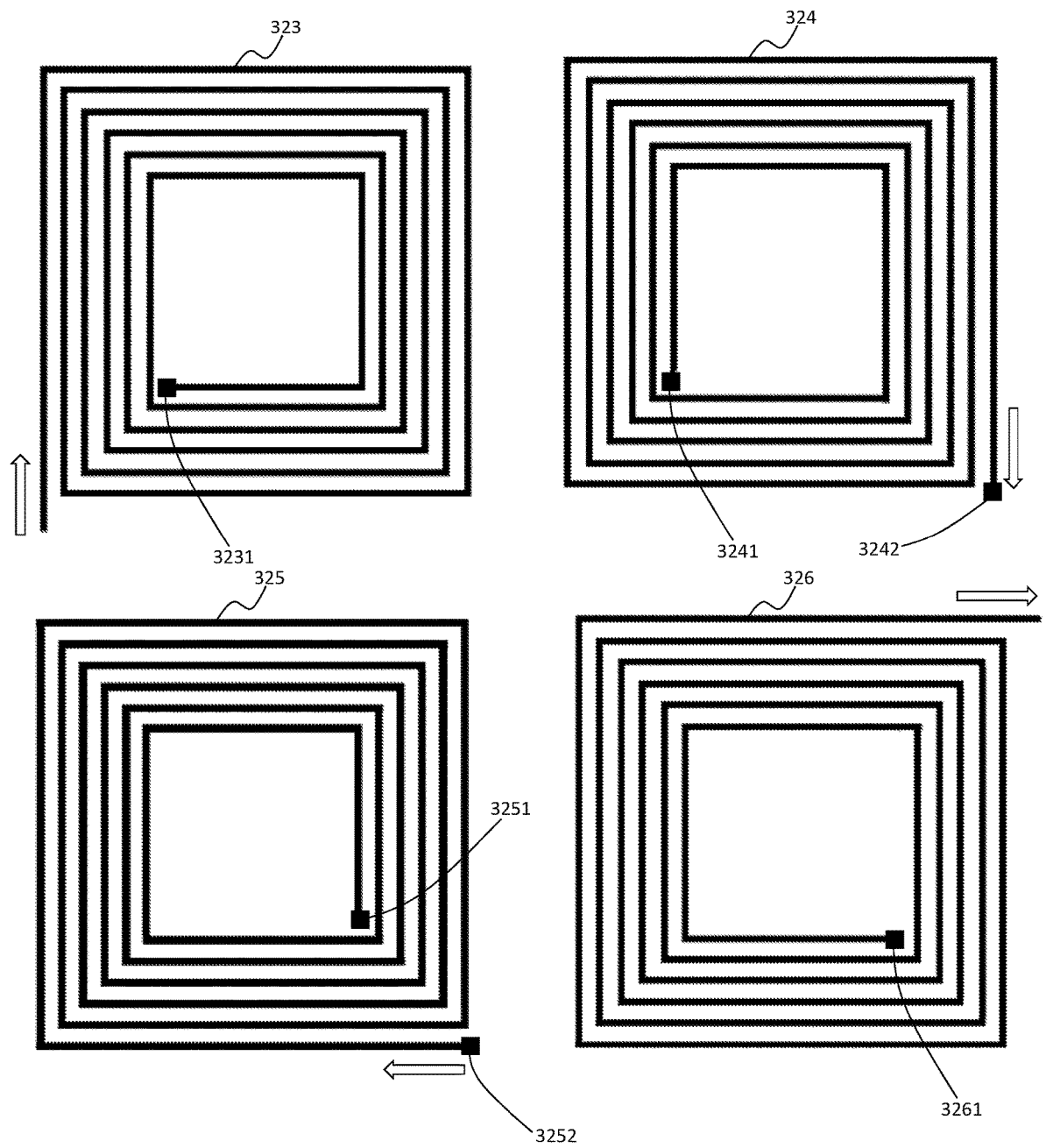
FIG. 13 is a schematic diagram of a planar coil of the embodiment of FIG. 12.

Please refer to FIG. 12 and FIG. 13. FIG. 12 shows a different structure of the planar coil module under the structure of the magnetic stimulation device having planar coil structure in FIG. 1. FIG. 13 is a sectional view of the planar coil module 300 of the present embodiment. The planar coil module 300 comprises a first planar coil 323, a second planar coil 324, a third planar coil 325, a fourth planar coil 326, an upper first insulating substrate 312, a middle first insulating substrate 313, a lower first insulating substrate 314, a first waterproof protective layer 333 and a second waterproof protective layer 334. The planar coils are parallel to one another. Adjacent two planar coils are electrically connected and formed on two sides of the same first insulating substrate. For example, the first planar coil 323 and the second planar coil 324 are electrically connected (electrically connected by plating a via hole 3121 formed on an upper first insulating substrate 312 using a plating material 340) and formed on two sides of the upper first insulating substrate 312; the second planar coil 324 and the third planar coil 325 are electrically connected (electrically connected by plating a via hole 3131 formed on a middle first insulating substrate 313 using a plating material 340) and formed on two sides of the middle first insulating substrate 313; the third planar coil 325 and the fourth planar coil 326 are electrically connected (electrically connected by plating a via hole 3141 formed on a lower first insulating substrate 314 using a plating material 340) and formed on two sides of the lower first insulating substrate 314. As mentioned above, the technical characteristics of the present invention are the current in the plurality of planar coils of the same planar coil module flows in the same rotational direction, and locations of the strongest magnetic field intensity generated by current of every planar coils are substantially aligned. In order to have a better understanding of the technical characteristics, please refer to FIG. 13. It is a schematic diagram of the first planar coil 323, the second planar coil 324, the third planar coil 325 and the fourth planar coil 326 viewed along the direction of an arrow in FIG. 12. The current flows in from the endpoint in the direction of the arrow on the left of the first planar coil 323 and flows out in a clockwise direction from an inner endpoint 3231 of the first planar coil 323. Since the inner endpoint 3231 and an inner endpoint 3241 of the second planar coil 324 are electrically connected, the current flows into the inner endpoint 3241 in a clockwise direction and flows out from an outer endpoint 3242 of the second planar coil 324. Then, the outer endpoint 3242 and an outer endpoint 3252 of the third planar coil 325 are electrically connected with. Therefore, current continues to flow clockwise to an inner endpoint 3251 of the third planar coil 325. Finally, since the inner endpoint 3251 and an inner endpoint 3261 of the fourth planar coil 326 are electrically connected, current flows into the inner endpoint 3261 in a clockwise direction and flows out from the endpoint of the fourth planar coil 326 near the top arrow. Each planar coil receives the adjusted output current to generate a corresponding varying intensity magnetic field. The current direction is the same in the 4 planar coils, so that the overall magnetic field intensity is the addition of the magnetic field intensity of 4 planar coils. Since the locations 350 of the strongest magnetic field intensity generated by current substantially aligned (vertical direction), magnetic field lines will not interfere with each other to reduce the overall magnetic field intensity. Overall, a three-dimensional structure is built to enhance the magnetic field intensity.

In other embodiments, if the number of the planar coil module 300 is more than one, end points of the outermost planar coil (the first planar coil 323 and the fourth planar coil 326) of adjacent two planar coil modules 300 are connected. Unconnected endpoints of the outermost planar coils of the first and the last planar coil modules 300 are directly electrically connected with the current switch 220.

Figure 14:
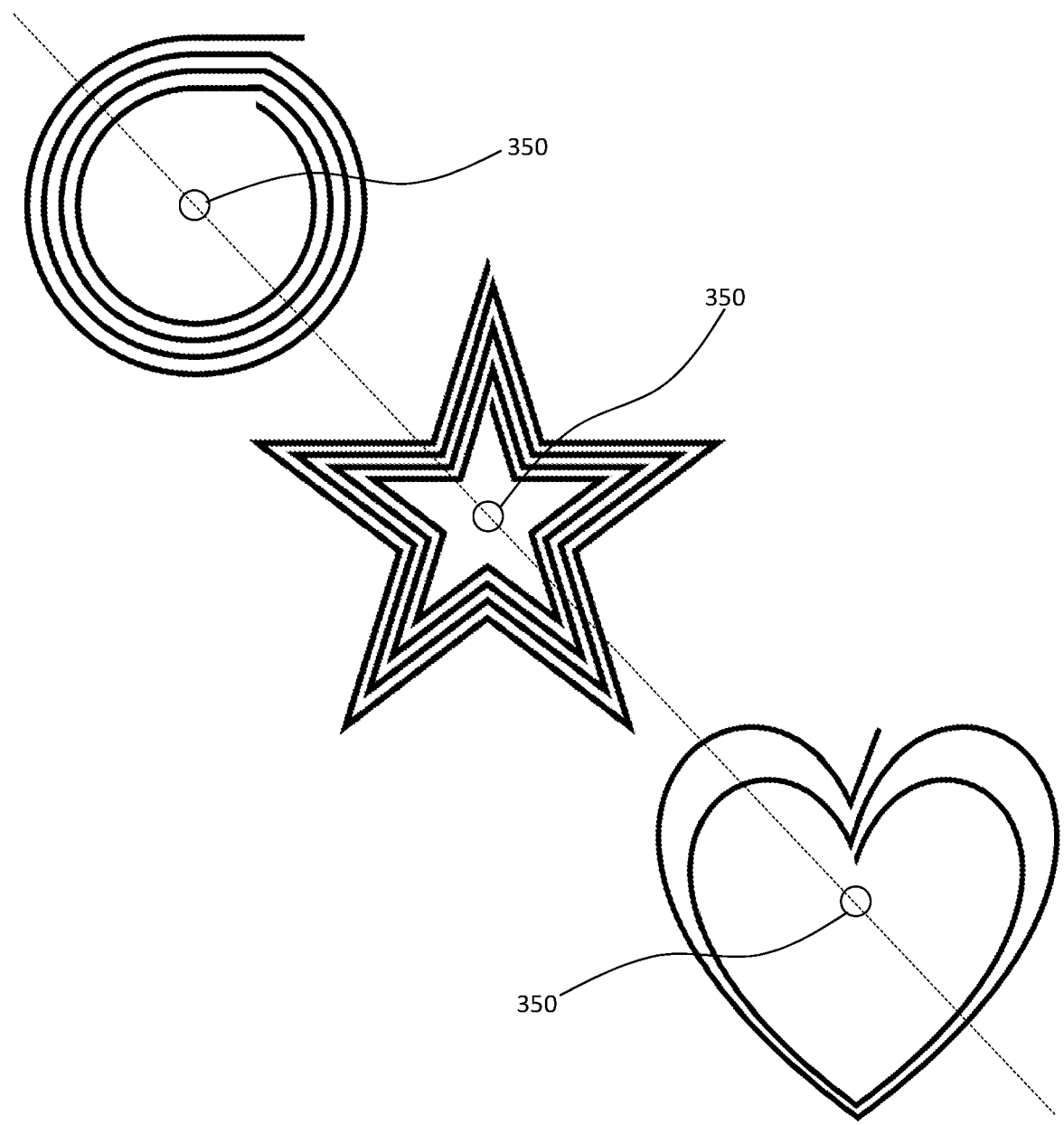
FIG. 14 shows three different shapes of electrically connected planar coil.

According to the present invention, a shape of the planar coil is not limited to square. The planar coil is formed around a specific pattern. As shown in FIG. 14, the planar coil module 300 comprises 3 kinds of different shaped planar coils electrically connected. In this embodiment, shapes of 3 planar coils are circle, star and heart, respectively. It should be noticed that the locations 350 of the strongest magnetic field intensity generated by current of all planar coils should be substantially aligned.

Although the present invention takes the human body as the target of magnetic stimulation, but in terms of application, it can also be extended to all organisms (animal and plants) for researches on extensive medical and biological operations.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A magnetic stimulation treatment device having coil structure, comprising:
a power supply module, providing electric power;
a current control module, electrically connected with the power supply module, comprising:
a signal generator, generating a current waveform signal; and
a current switch, electrically connected with the signal generator, adjusting a waveform of current from the power supply module with the current waveform signal to form an adjusted output current; and
at least one planar coil module, comprising:
at least one first insulating substrate; and
a plurality of planar coils laminated in parallel to one another, wherein adjacent two planar coils are electrically connected and formed on two sides of the same first insulating substrate,
wherein, if the number of the planar coil module is one, end points of outermost two planar coils are directly electrically connected with the current switch to form a loop; if the number of the planar coil module is more than one, end points of the outermost planar coils of adjacent two planar coil modules are connected and unconnected endpoints of the outermost planar coils of the first and the last planar coil modules are directly electrically connected with the current switch; each of the plurality of planar coils receives the adjusted output current to generate a corresponding varying intensity magnetic field, the current in the plurality of planar coils of the same planar coil module flows in the same rotational direction, and locations of the strongest magnetic field intensity generated by current of every planar coils are substantially aligned, wherein an electric stimulation magnetic field of the at least one planar coil module generated by the adjusted output current ranges between 0 to 1000 Gauss, wherein the adjacent two planar coils are electrically connected by plating a via hole formed on the first insulating substrate with a plating material.

2. The magnetic stimulation treatment device having coil structure according to claim 1, wherein the at least one planar coil module further comprises a ferrite core, located on location of the strongest magnetic field intensity generated by current of the at least one planar coil module, enhancing overall magnetic permeability of the at least one planar coil module.

3. The magnetic stimulation treatment device having coil structure according to claim 1, wherein the current control module further comprises a current limiter, electrically connected between the power supply module and the current switch, limiting the current from the power supply module.

4. The magnetic stimulation treatment device having coil structure according to claim 1, wherein the power supply module comprises at least one primary battery, at least one secondary battery or a power supply.

5. The magnetic stimulation treatment device having coil structure according to claim 1, wherein the signal generator is a waveform generator, a pulse generator or a clock generator.

6. The magnetic stimulation treatment device having coil structure according to claim 1, wherein a waveform of the current waveform signal is a sine wave, a half sine wave, a pulse wave or a fixed waveform.

7. The magnetic stimulation treatment device having coil structure according to claim 1, wherein each of the plurality of planar coils is made by etching metal foil, winding metal wire or printing conductive adhesive.

8. The magnetic stimulation treatment device having coil structure according to claim 1, wherein a material of the first insulating substrate is bakelite, cotton paper, epoxy resin, glass cloth, glass fiber, phenolic resin, glass, polyimide or polyester.

9. The magnetic stimulation treatment device having coil structure according to claim 1, further comprising a plurality of electrical connection modules, electrically connected with the at least one planar coil module and the current switch to form a loop, wherein each electrical connection module comprises:

a second insulating substrate;

at least one wire, formed on the second insulating substrate; and a waterproof protective layer, covering the at least one wire and the second insulating substrate to protect the at least one wire and avoid damages from external water.

10. The magnetic stimulation treatment device having coil structure according to claim 9, wherein a material of the second insulating substrate is polyimide or polyester.

11. The magnetic stimulation treatment device having coil structure according to claim 9, wherein a material of the waterproof protective layer is polyimide film or polyethylene terephthalate film.

12. The magnetic stimulation treatment device having coil structure according to claim 1, wherein each of the plurality of planar coils is formed around a specific pattern.

* * * * *